US00PP10979P

United States Patent [19]

van den Bosch

[11] Patent Number: Plant 10,979

[45] Date of Patent: Jun. 29, 1999

[54] HYPERICUM PLANT NAMED 'DUAL FLAIR'

[75] Inventor: Bernard Renee van den Bosch, Rijnsburg, Netherlands

[73] Assignee: H. and B.R. van den Bosch B.V., Rijnsburg, Netherlands

[21] Appl. No.: 09/004,125

[22] Filed: Jan. 7, 1998

[51] Int. Cl.[6] ..... A01H 5/00

[52] U.S. Cl. ..... Plt./226

[58] Field of Search ..... Plt./226, 263

[56] References Cited

U.S. PATENT DOCUMENTS

P.P. 568 3/1943 Grullemans ..... Plt./226

OTHER PUBLICATIONS

GTITM UPOVROM Citation for 'Dual Flair' as per NL PBR 'SJK0002', Feb. 15, 1994.

GTITM UPOVROM Citation for 'Dual Flair' as per DE PBR 'HAN00001', Nov. 30, 1994.

GTITM UPOVROM Citation for 'Dual Flair' as per IL PBR '02443', Oct. 1, 1995.

GTITM UPOVROM Citation for 'Dual Flair' as per NZ PBR 'HYP001', Aug. 22, 1997.

GTITM UPOVROM Citation for 'Bosadua' as per AU PBR '97230', Sep. 26, 1997.

*Primary Examiner*—Howard J. Locker
*Assistant Examiner*—Kent L. Bell
*Attorney, Agent, or Firm*—C. A. Whealy

[57] ABSTRACT

A distinct cultivar of Hypericum plant named 'Dual Flair', characterized by its early flowering; dark reddish brown berries; dark green leaves; and excellent postproduction longevity.

2 Drawing Sheets

The present invention relates to a new and distinct cultivar of Hypericum plant, botanically known as *Hypericum androsaemum*, commonly referred to as Saint John's Wort, commercially used as a cut flower, and hereinafter referred to by the cultivar name 'Dual Flair'.

The new cultivar is a product of a planned breeding program conducted by the inventor in Rijnsburg, The Netherlands. The objective of the breeding program was to develop cut Hypericum varieties with attractive berry color, early flowering, long flowering stem length, and large berry size. The new cultivar originated from a cross made by the inventor in 1984 of two proprietary seedlings. The proprietary selection code number 83 was the female, or seed, parent, and the proprietary selection code number 71 was the male, or pollen, parent. The cultivar 'Dual Flair' was discovered and selected by the inventor in August, 1985 as a flowering plant within the progeny of the stated cross in a controlled environment in Rijnsburg, The Netherlands.

Asexual propagation of the new cultivar by cuttings taken at Rijnsburg, The Netherlands, has shown that the unique features of this new Hypericum plant are stable and reproduced true to type in successive generations.

The following traits have been repeatedly observed and are determined to be the unique characteristics of 'Dual Flair'. These characteristics in combination distinguish the new Hypericum plant as a new and distinct cultivar:

1. Early flowering; plants flower about 13 weeks after planting.
2. Dark reddish brown berries.
3. Dark green leaves.
4. Excellent postproduction longevity; cut stems typically last about 12 days.

The new Hypericum can be compared to the nonpatented commercial cultivar, 'Excellent Flair'. In side-by-side comparisons conducted in Rijnsburg, The Netherlands, plants of the new Hypericum were shorter, had narrower and redder berries, and flowered earlier than plants of the cultivar 'Excellent Flair'. In addition, leaves of plants of the new Hypericum are dark green whereas leaves of plants of the cultivar 'Excellent Flair' are blue green in color.

The new Hypericum can be compared to the cultivar, 'Bosakin' (U.S. Plant patent application Ser. No. 09/004,124). In side-by-side comparisons conducted in Rijnsburg, The Netherlands, plants of the new Hypericum were shorter, had smaller and more brown berries, and flowered earlier than plants of the cultivar 'Bosakin'.

Plants of the new Hypericum have not been observed under all possible environmental conditions. The phenotype may vary significantly with variations in environment such as temperature, light or fertility level, without, however, any variance in genotype.

BRIEF DESCRIPTION OF PHOTOGRAPHS

The accompanying colored photographs illustrate the new Hypericum plant, showing the colors as true as it is reasonably possible to obtain in colored reproductions of this type.

The photograph at the top of the first sheet comprises a view of typical flowering plants of the new Hypericum plant under commercial production in Rijnsburg, The Netherlands.

The photograph at the bottom of the first sheet comprises a close-up view of typical leaves of plants of the new Hypericum.

The photograph at the top of the second sheet comprises a close-up view of typical flowers of plants of the new Hypericum.

The photograph at the bottom of the second sheet comprises a close-up view of typical berries of plants of the new Hypericum. Flower, fruit and foliage color in these photographs may appear different from the actual colors due to light reflectance.

DETAILED BOTANICAL DESCRIPTION

The following observations, measurements, values, and comparisons describe plants grown in Rijnsburg, The Netherlands, under outdoor commercial production practice. In the following description, color references are made to The Royal Horticultural Society Colour Chart except where general terms of ordinary dictionary significance are used.

Classification:

*Botanical.*—*Hypericum androsaemum* cultivar 'Dual Flair'.

*Commercial.*—Cut Hypericum.

Parentage:

*Female parent.*—*Hypericum androsaemum* proprietary selection code number 83.

*Male parent.*—*Hypericum androsaemum* proprietary selection code number 71.

Propagation:

*Type.*—Cuttings.

*Rooting habit.*—Fine, fibrous and well-branched.

Plant description:

*Form.*—Upright woody shrub with erect lateral branches, branch angle about 45°.

*Growth habit.*—Moderately vigorous. Freely branching and dense growth.

*Plant height.*—About 45 cm.

*Stem and lateral branch color.*—Light green with reddish overtones.

*Foliage description.*—Leaves arranged oppositely, single, sessile, and generally symmetrical. Length: About 8.4 cm. Width: About 5 cm. Shape: Ovate with acute apex and obtuse base. Margin: Entire. Texture: Smooth, leathery. Color: Upper side: Dark green, 137A. Under side: Light green, 137C.

Flower description:

*Flower type and habit.*—Large golden yellow flowers arranged in apical compound umbels. Early flowering; plants flower about 13 weeks after planting. Natural flowering season in The Netherlands is early autumn, typically August and September. Flowers are not fragrant.

*Postproduction longevity.*—Cut flowers are typically harvested when all flowers have developed berries. From flowers to berries takes about three weeks. Postproduction longevity of cut stems of the new Hypericum typically is about 12 days.

*Flower diameter.*—About 3 cm.

*Petals.*—Quantity: Typically five per flower. Length: About 1.6 cm. Width: About 8 mm. Shape: Elliptic, obtusely rounded, slightly asymmetrical. Margin: Entire. Color: 14A to 15A.

*Sepals.*—Quantity: Typically five per flower. Size: Three larger sepals, about 8 by 5 mm; and two smaller sepals, about 6 by 4 mm. Shape: Elliptic with nearly rounded apex, often slightly asymmetrical. Color: Upper side: Green, 137B, with brownish red apex. Under side: Light green, 137C, with faint reddish streaks.

*Peduncles.*—Strength: Strong. Aspect: Erect. Length: About 2 cm. Color: 176A/178A to 181A.

*Reproductive organs.*—Stamens: Quantity: About 80 per flower. Stamen shape: Slightly fan-shaped. Stamen color: Yellow. Anther color: Yellow. Pistils: Style quantity: Three per flower. Style color: Light greenish yellow. Stigma color: Reddish brown. Ovary color: Pale green.

*Fruit description.*—Shape: Oval. Length: About 1.2 cm. Diameter: About 8 mm. Color: Reddish brown, 178A/185A.

Disease resistance: Resistance to pathogens common to Hypericum has not been observed under commercial production conditions.

It is claimed:

1. A new and distinct Hypericum plant named 'Dual Flair', as illustrated and described.

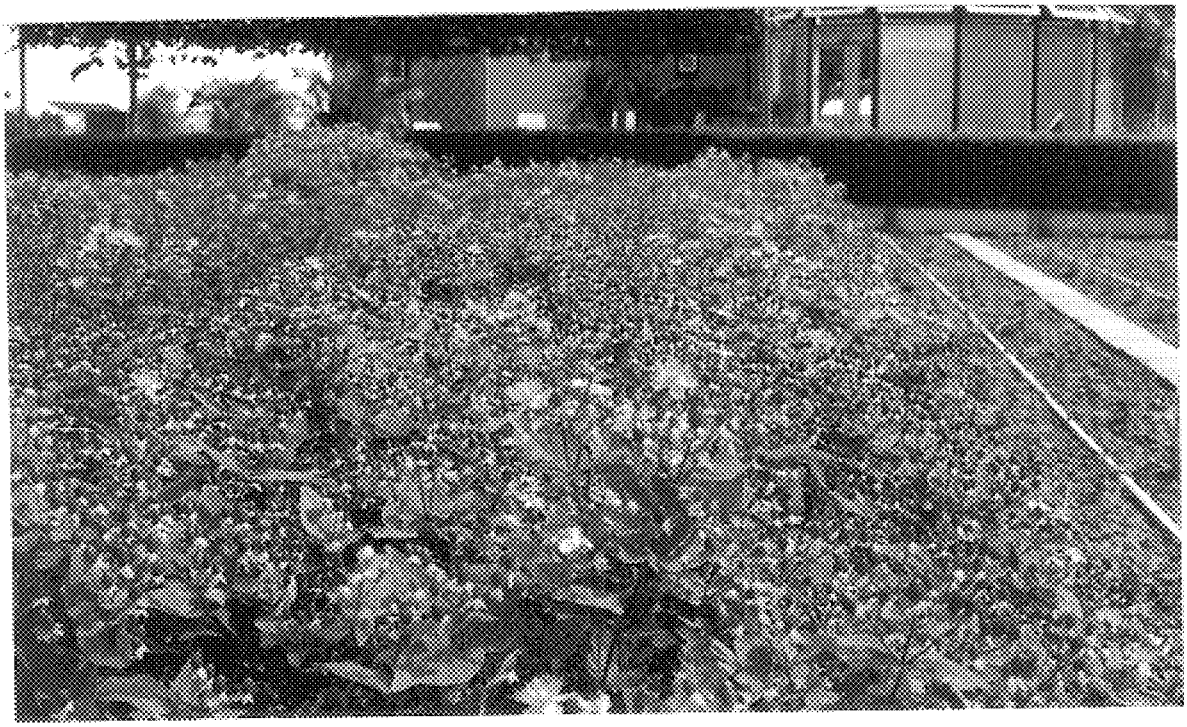
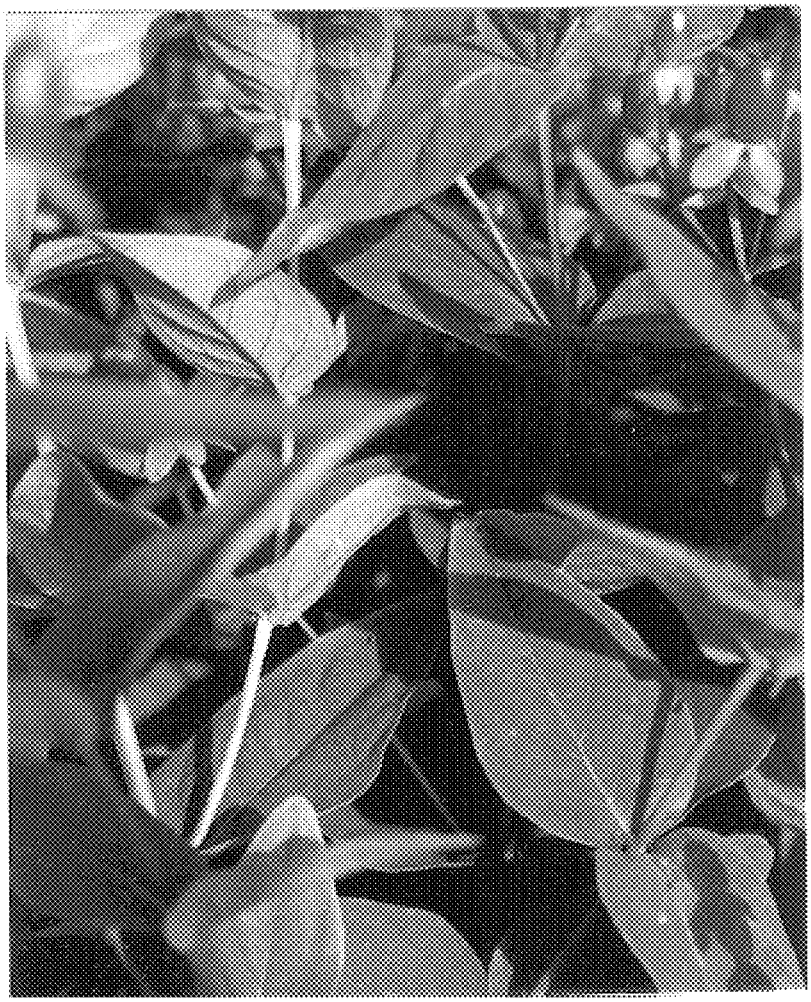

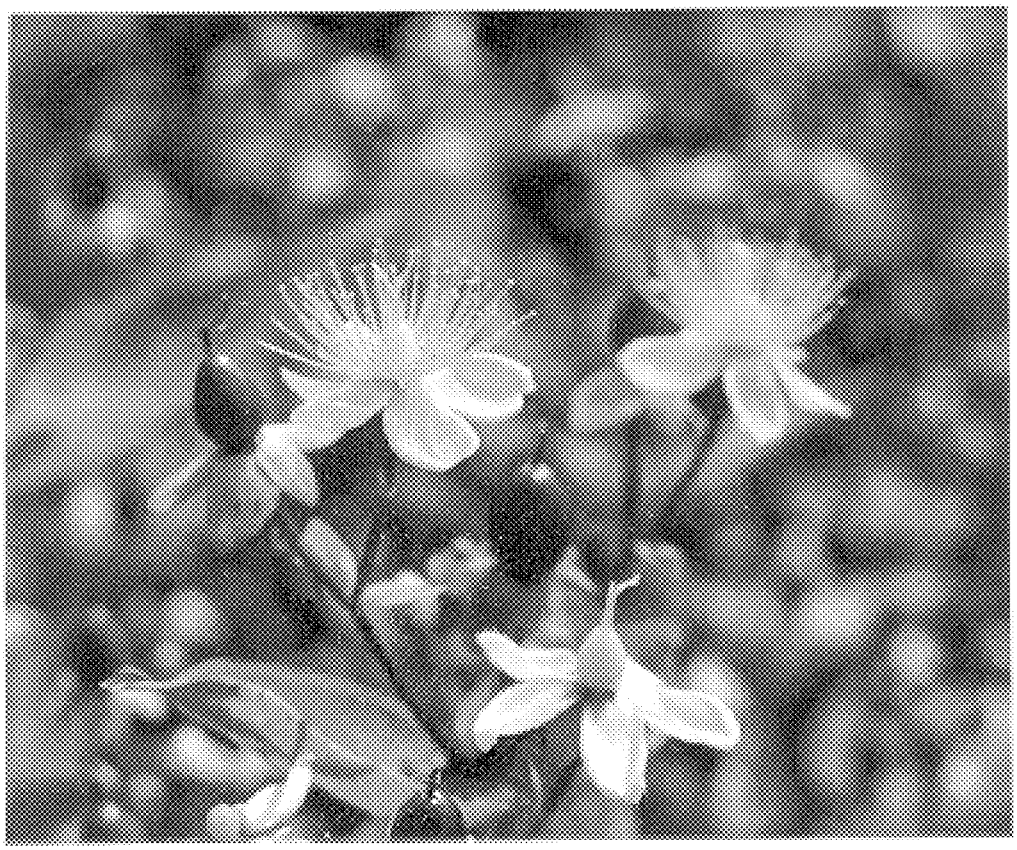
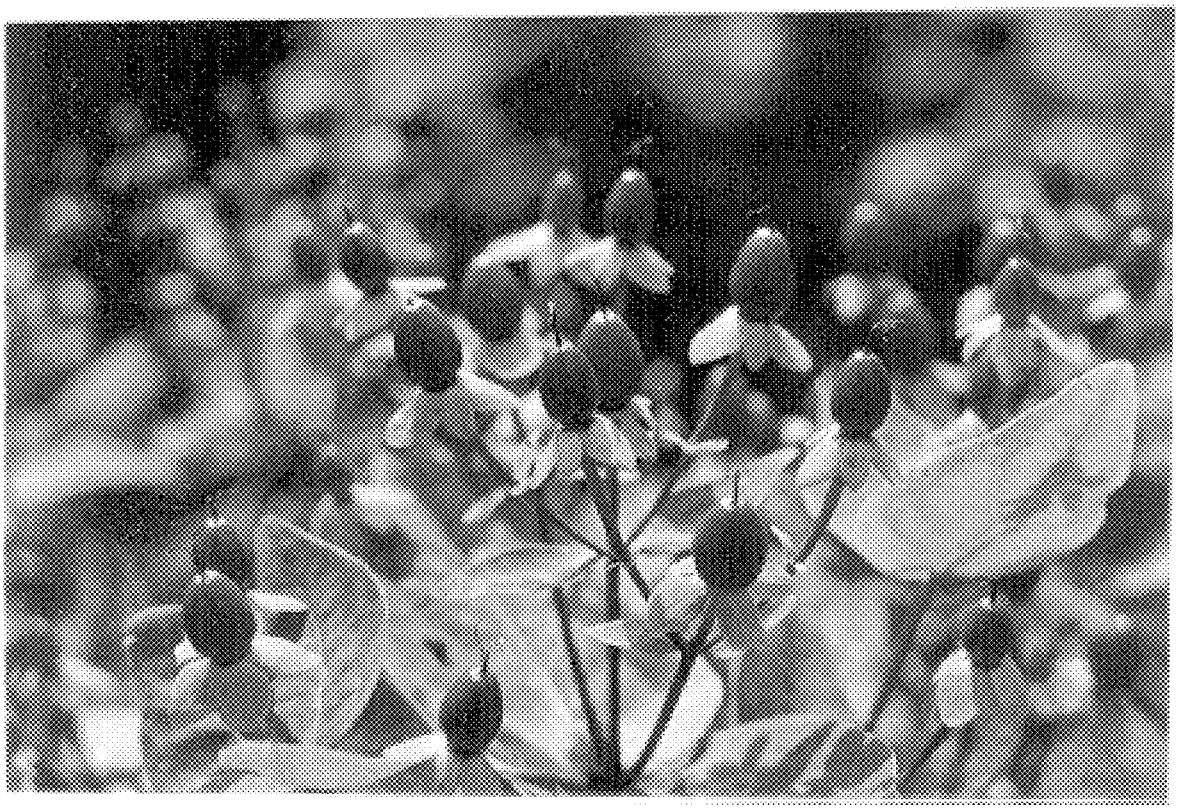

* * * * *